United States Patent
Modi et al.

(10) Patent No.: US 9,714,275 B2
(45) Date of Patent: Jul. 25, 2017

(54) CANCER ANTIGEN

(75) Inventors: Indravadan Ambalal Modi, Ahmedabad (IN); Rajiv Indravadan Modi, legal representative, Ahmedabad (IN); Bakulesh Mafatlal Khamar, Ahmedabad (IN); Chandreshwar Prasad Shukla, Ahmedabad (IN); Vipul Sitaram Thakkar, Ahmedabad (IN); Nirav Manojkumar Desai, Ahmedabad (IN)

(73) Assignee: Cadila Pharmaceuticals Ltd. (IN)

( * ) Notice: Subject to any disclaimer, the term of this patent is extended or adjusted under 35 U.S.C. 154(b) by 57 days.

(21) Appl. No.: 14/130,504

(22) PCT Filed: Jul. 4, 2012

(86) PCT No.: PCT/IB2012/053396
§ 371 (c)(1),
(2), (4) Date: Apr. 17, 2014

(87) PCT Pub. No.: WO2013/005164
PCT Pub. Date: Jan. 10, 2013

(65) Prior Publication Data
US 2014/0294896 A1    Oct. 2, 2014

(30) Foreign Application Priority Data
Jul. 5, 2011   (IN) .......................... 1929/MUM/2011

(51) Int. Cl.
*A61K 39/00*   (2006.01)
*C07K 14/47*   (2006.01)

(52) U.S. Cl.
CPC ...... *C07K 14/4748* (2013.01); *A61K 39/0011* (2013.01)

(58) Field of Classification Search
None
See application file for complete search history.

(56) References Cited

U.S. PATENT DOCUMENTS

| 7,972,609 B2 * | 7/2011 | Khamar | 424/248.1 |
| 2008/0131458 A1 * | 6/2008 | Khamar | A61K 39/39 424/204.1 |
| 2011/0129822 A1 | 6/2011 | Shen | |

FOREIGN PATENT DOCUMENTS

WO   WO 2006/114680   * 11/2006

OTHER PUBLICATIONS

Matsuzaki et al (Oncology, 2000, 59:336-343, abstract only).*
Sur et al (J Indian Med Assoc, 2003, 101:118-120).*
Belani et al (Journal of Clinical Oncology, 2011 ASCO Annual Meeting Abstracts Part I, vol. 29, No. 15 Suppl (May 20 Supplement) Abstract 7501).*
Khamar et al (Cancer Research, May 2008, 68:abstract 1015).*
Kultima et al (BMC Bioinformatics, 2006, 7:475, internet pp. 1-27).*
Sambrook et al. (Molecular Cloning, 2nd edition, Cold Spring Harbor Press, 1989, p. 18.47).*
Invitrogen™ product information sheet for protein standards and ladders (printed 2008).*
Lee et al (Society for Investigative Dermatology, 2011, 131:1701-1709).*
McGee et al (Cancer biotherapy & Radiopharmaceuticals, 1999, 14:203-208).*
Jimeno et al (Mol Cancer Ther, 2007, 6:1509-1516).*
Bhutia et al (Plos One, 2013, 8:e53436, internet pp. 1-13).*
Yang et al (World J Gastroenterol 2003, 9:2828-2831).*
Khamar et al, Cancer Research, 2012, 72(8 Suppl): Abstract nr 1582.*
Rakshit et al (Int J Cancer, 2012, 130:865-875).*
Halder et al (Cancer Biol Ther. Sep. 21, 2015, abstract only).*
International Search Report issued by the PCT for the PCT Application PCT/IB2012/053396 on Jan. 11, 2013. (5 pages).

* cited by examiner

*Primary Examiner* — Laura B Goddard
(74) *Attorney, Agent, or Firm* — Burns & Levinson, LLP (57) ABSTRACT

Cancer cells when treated with cisplatin, paclitaxel, gemcitabine, Mycobacterium w or combination there of shows altered protein profile. Thus altered protein profile has at least one protein commonly expressed or over expressed. The commonly expressed or over expressed protein induces immune response specific to cancer cells (homologue and hetrologus) of tissue/organ of origin. The immune response generated by administration of commonly expressed or over expressed antigen not reactive to normal cells and cancer cells or different tissue/organ of origin.

6 Claims, 4 Drawing Sheets

Fig 1: Induction of cell mediated immune response by the commonly expressed/over expressed cancer antigen Loading Pattern Lane 1: Prestained Mol wt marker Lane 2: Serum of mice immunized with treated Mia-pa-ca 2 cells expressing 45 KDa protein as primary antibody Lane 3: Serum of normal mice as primary antibody Fig 2: Induction of Humoral immune response by the commonly expressed/over expressed cancer antigen Figure 3: Comparison between No treatment and vaccine treatment group Figure 4: Immune response generated by commonly expressed/over expressed protein is specific to cancerous tissue /organ of origin.

CANCER ANTIGEN

FIELD OF INVENTION

The present invention relates to antigen/s of cancer vaccines having immunogenicity against cancer that is specific to tissue/organ of origin for use in management of cancer. The invention also provides method of preparing the same.

BACKGROUND

Cancer is caused by rapidly dividing cells. It is a major cause of morbidity and mortality. Cancer arises from a tissue/organ. In spite of the fact that it arises from a single tissue/organ, the cells are not identical (homologous). Cancer is being treated by surgical removal, radiotherapy and/or chemotherapy. The passive immunotherapy in form of antibodies is also found to be useful. Presence of heterogeneous cells in a cancer arising from a single tissue/organ is known to be responsible to poor response to cancer therapies other than surgical therapy. These are more important for treating the cancers using immunotherapy.

Active immunotherapy is being tried in form of vaccine for management of cancer. Active immunotherapy requires use of antigen specific to cancer being treated. Some of the Cancer specific antigens include matrix metalloproteinase inhibitors, epidermal growth factor, gastrin, whole cancer cells, Heat Shock Proteins etc.

Several methods have been proposed for producing immunogenic cancer vaccine using whole cells. The immune response generated by cancer vaccine often causes autoimmunity or toxicity (Blood-2011-01-325-266).

Thus there is a need to have cancer antigen which induces immune response against cancer antigens but not against normal cells (Autoimmunity).

Cancer cells when used as an antigen either lack immunogenicity or generate poor immune response. It is known that anthracyclin and Oxliplatin improves immunogenicity of cancer cells as reported by Laurence Zitvogel et al in Clin Cancer Res, 2010, 16(12):3100-4. "In response to some chemotherapeutic agents (such as anthracyclines and oxaliplatin) and ionizing irradiation, tumor cells undergo immunogenic apoptosis, meaning that they trigger a protective immune response when they are injected subcutaneously in the absence of any adjuvant into immunocompetent mice (*J Exp Med* 2005; 202: 1691-701; *Nat Med* 2007; 13: 54-61; *Immunol Rev* 2007; 220: 22-34; *Nat Med* 2007; 13: 1050-9; *Nat Med* 2009; 15:1170-8; *Cell Mol Immunol* 2009; 6: 469-75; *Cancer Immunol Immunother* 2010; 59: 769-77.) In contrast, cells succumbing in response to other anticancer drugs (such as alkylating agents and cisplatin) fail to trigger such an immune reaction (*J Exp Med* 2005; 202: 1691-701.)."

The challenge is to generate the immune response specific against cancer cells without being reactive to normal cells and cancer cells of different tissue/organ of origin.

Thus there is an unmet need to provide a cancer vaccine having immunogenicity to the heterogeneous population of cells originating from same tissue/organ with no reactivity to the normal cells.

OBJECT OF INVENTION

The main object of present invention is to provide antigen/s for cancer vaccine/s Another object of present invention is to provide antigen for cancer vaccine that elicits immune response against cancer cells (homologous as well as heterogeneous cancer cells) of tissue/organ of origin.

It is yet another object to provide cancer antigen for malignant tumor/s that stimulate the cell mediated immune response against cancer cells (homologous as well as heterogeneous cancer cells) of tissue/organ of origin.

It is yet another object to provide cancer vaccine for malignant tumor/s that stimulate humoral immune response against cancer cells (homologous as well as heterogeneous cancer cells) of tissue/organ of origin.

Yet another object of present invention is to provide an antigen for cancer vaccine for use in treatment of malignant tumor/s.

It is yet another object of invention to provide method of preparing the antigen for cancer vaccine.

SUMMARY OF INVENTION

For the purpose of present invention cancer cells may be isolated from tumor tissues. Any cancer cell originating from established cell lines available commercially or new primary cancer cells obtained from patients are used for the purpose of the present invention.

Surprisingly cancer cells treated with cisplatin, paclitaxel, gemcitabine, *Mycobacterium* w or combination there of shows altered protein profile. Further surprisingly the protein profiles of treated cell is found to have at least one protein common (commonly expressed/over expressed) irrespective agent used for treatment e.g. *Mycobacterium* w, cisplatin, paclitaxel, gemcitabine. This surprising observation is despite of the fact that each one is having different activities. This protein is found to be differently expressed protein following above treatments as per present invention.

The commonly expressed protein as per present invention is found to be immunogenic and induces immune response reactive against cancer cells from which it is derived (homologous) as well as cancer cells of same tissue/organ but with different cell characteristic (heterologus).

As per the invention when a pancreatic cancer cell line treated with any one of the above mentioned agent results in expression of a protein which elicits immune response against same (homologus) cells as well as different (heterologus) cells as long as their origin is same tissue/organ, e.g. protein expressed after treatment of Mia-pa-ca-2 cell line will induce immune response against Mia-pa ca-2 cells (homologus) as well as Panc-1, AsPc-1, SW 1990 etc. (hetrologus). The immune response generated is cell mediated as well as humoral in nature.

The immune response so generated is capable of providing prophylactic as well as therapeutic effects against pancreatic cancer.

The immune response generated using pancreatic cancer cell line fails to generate immune response against other cancer. Administration of the protein/s is found to be safe in mammals.

DETAILED DESCRIPTION

It is observed that when cancer cells are treated with *Mycobacterium* w (Mw) there is change in protein profile of cancer cells. The change in protein profile is associated with abundance of a single protein band as observed by SDS page analysis.

Surprisingly the same protein is found to be expressed when cells are treated with Cisplatin, Paclitaxel, gemcitabine. The protein which is so expressed is defined as commonly expressed/overexpressed protein.

The protein so expressed can be isolated using known methods as described in Current Protocols in Protein Science by John E. Coligan et al.

Surprisingly this protein is found to generate immune response against homologous as well as heterogeneous cancer cells specific to tissue/organ of origin. The protein does not generate immune response against normal cells/tissues when administered to mammals.

Surprisingly it is also observed that the treatment of cancer cells with compounds such as cisplatin, paclitaxel and gemcitabine also results in expression of the protein which is expressed, when cells are treated with *Mycobacterium* w.

Thus as per the present invention the protein(s) which is commonly expressed/over-expressed by treatment of cancer cells with Mw, cisplatin, paclitaxel and gemcitabine or combination there of generates immune response against homologous as well as hetrologenous cancer cells, specific to tissue/organ of origin.

The commonly expressed/over-expressed protein that induces immune response is isolated from cancer cell/s. For the purpose of present invention it is not necessary for treatment with various agents to induce death of cancer cells. The cells are not required to be live for isolation of the commonly expressed protein.

The common protein of present invention also induces the immune response specific to the heterogeneous cancer cells specific to tissue/organ.

Administration of the common protein of present invention induces cell mediated immune response. The common methods deployed for measurement of cell mediated immune response are FACS, ELISPOT, and Effector function, etc.

Administration of the common protein of present invention induces humoral immune response. The common methods deployed for the purpose are FACS, Western blot, Elisa etc.

The efficacy the cancer antigen is determined by its ability to induce immune response against homologous as well as hetrologenous cancer cells, specific to tissue/organ of origin.

The efficacy of the cancer vaccine to induce immune response was studied by determining cell mediated immune response as measure of increase in number of cells producing interferon gamma in response to antigen by ELISPOT.

The efficacy of the cancer vaccine to induce immune response was studied by determining humoral immune response from the sera of mice, immunized with cells expressing/over expressing the antigen and mice immunized with the antigen alone by presence of specific antibody reactive to antigen.

Similarly, the induced immune response to heterogeneous cancer cells specific to tissue/organ was determined. The heterogeneous response was evaluated for both cell mediated using interferon gamma ELISPOT and humoral response using western blot.

The cell lines for the purpose of invention can be procured from various repositories like American Type Culture Collection, USA; Cell bank Australia, Australia; Coriell Cell Repositories, New Jersey USA; European Collection of Cell Cultures (ECACC), UK; German Collection of Microorganisms and Cell Cultures, Germany; Japanese Collection of Research Bioresources (JCRB), Japan; German Collection of Microorganisms and Cell Cultures, Germany; Korean Cell bank, Korea; RIKEN Biresource Centre, Japan; Human Genetics Resource Center, USA; National Centre for Cell Science, India; MMRRC: Mutant Mouse Regional Resource Centers, USA; National Human Neural Stem Cell Resource, USA; UK Stem Cell Bank, UK and NCCS in India.

The methods for harvesting cancer cells and preserving them or propagating them are well known. These methods can be used for autologus as well as allogenic cells. These or new cell lines or specific cancer cells can be isolated as described by Eton O, et al. (Clinical cancer research, March 1998, Vol. 4, 619-627). Fresh tumor was collected at the time of surgery from frozen section laboratory and fragmented by slicing, to maximize the yield of viable tumor cells for vaccine preparation, the bulk of tumor was dissociated using collagenase type 1 (2 mg/ml) and type IV DNase (0.4 mg/ml) Sigma chemical Co., St Louis, Mo.; ref 25. These enzymes can alter the immunogenicity of the resulting cell preparation. The dissociated cells were washed in HBSS and gentamycin and resuspended in equal volumes of HBSS and chilled 10% DMSO+4% human serum albumin. Aliquots containing $1.5-2\times10^7$ viable tumor cells stored under liquid Nitrogen.

Following process describes process for obtaining commonly expressed protein as per present invention 1. Cancer cells are suspended in appropriate cell culture media like DMEM, EMEM, Hanks F12 etc.
2. To these any of the following agents are added such as cisplatin, paclitaxel, gemcitabine and *Mycobacterium* w
3. All the agents are known to kill cancer cells, how ever for the purpose of this invention to obtain commonly expressed protein it is not necessary to kill the cancer cells by treatment with any or all of the agents. Similarly killing of cells do not result in loss of properties of cancer cells express 'common protein' of interest nor change its immune characteristics.
4. Following table provides preferable amount of various agents to be used

| Sr No | Agent | Prefered Amount |
|---|---|---|
| 1 | Cisplatin | 0.1 to 100 microgram/ml |
| 2 | Paclitaxel | 5 to 500 microgram/ml |
| 3 | Gemcitabine | 10 to 1000 nM |
| 4 | Mycobacterium w | 1:10 to 1:1000 |

5. The cells are harvested after above mentioned treatment
6. Protein profile of harvested cells is generated using known methods like electrophoresis, HPLC etc.
7. The 'commonly expressed protein is identified by over lapping protein profiles obtained by treatment using various agents as mentioned above
8. The identified protein can be obtained on large scale using methods of protein purification.

The cancer cells obtained as above were treated with Mw Cells, in ratio of ranging from 1:10 to 1:1000, preferably in 1:100. The treatment was carried out in suitable medium preferably in serum free growth supporting medium. The treatment was performed at temperatures ranging between 20-40° C. preferably at 37° C. The treated cells were lysed by one of the methods known in art and SDS-PAGE was run to obtain proteomic profile. Thus obtained profile was compared with the untreated cell protein profile. The differentially expressed protein band pattern was noticed.

The cancer cells were treated with Cisplatin, at concentration ranging from 0.1 µg/ml to 100 µg/ml preferably at 5 µg/ml. The treatment was carried out in suitable medium preferably in serum free growth supporting medium. The treatment was performed at temperatures ranging between 20-40° C. preferably at 37° C. The treated cells were lysed by one of the methods known in art and SDS-PAGE was run to obtain proteomic profile. Thus obtained profile was compared with the untreated cell protein profile. The differentially expressed protein band pattern was noticed.

The cancer cells were treated with paclitaxel, at concentration ranging from 5 µg/ml to 500 µg/ml, preferably at 5 µg/ml. The treatment was carried out in suitable medium preferably in serum free growth supporting medium. The treatment was performed at temperatures ranging between 20-40° C. preferably at 37° C. The treated cells were lysed by one of the methods known in art and SDS-PAGE was run to obtain proteomic profile. Thus obtained profile was compared with the untreated cell protein profile. The differentially expressed protein band pattern was noticed.

The cancer cells were treated with gemcitabine, at concentration ranging from 10 nm to 1000 nm, preferably at 800. The treatment was carried out in suitable medium preferably in serum free growth supporting medium. The treatment was performed at temperatures ranging between 20-40° C. preferably at 37° C. The treated cells were lysed by one of the methods known in art and SDS-PAGE was run to obtain proteomic profile. Thus obtained profile was compared with the untreated cell protein profile. The differentially expressed protein band pattern was noticed.

The altered protein profiles obtained for each of the above treatment were matched with each other. The commonly expressed/over expressed protein/s was noted/identified at between 40-50 KDa in Mia-pa-ca-2 cancer cells.

The treated and untreated cancer cells were re-suspended in PBS, pH 6.5 to 7.5. The cells were sonicated for 500-1500 seconds programmed for 5-15 sec on and 5-15 sec off, preferably sonicated for 900 seconds programmed for 9 sec on and 10 sec off. The total protein estimation by Lowry protein estimation method was performed for lysate. The total protein was calculated and 20 microgram protein/lane was loaded on the gel, 5-20% acrylamide gel was used for isolation of the protein preferably 10% acrylamide gel with surfactant such as but not restricted to SDS was used. The gel was run at a constant voltage of 100 to 300V, preferably 200 V for 30-90 min, preferably 60 min. The gel was stained with coomassie Blue R250 staining solution for 15-60 min and de-stained with de-staining solution (40% Methanol+ 10% Acetic acid+50% water) till the background was clear and bands visible on gel. The protein profile obtained was matched band by band and commonly expressed/over expressed protein by treatment with Mw, cisplatin, paclitaxel, and gemcitabine were noted.

After identification, the gel having band of interest was cut in to pieces and then eluted in elution buffer (20 mM Tris —Cl, pH 7.7, 150 mM NaCl, 0.2% SDS, 2 mM EDTA) and kept on a shaker for agitation at RT for a minimum of 6-8 hours or overnight. The supernatant was collected and ice-chilled acetone (1:4, protein:acetone) was added and kept at −20° C. for 1-2 hours for precipitation. The precipitate was centrifuged at 15000×g for 45 min at 4° C. Obtained pellet was washed with acetone (Acetone:water, 4:1) and resuspended in desired volume of PBS. The total protein was estimated by Lowry assay and its specificity was analyzed by using in-house mouse serum containing antibody against the protein of interest. 2-D gel electrophoresis was done to identify this differential expressed protein. The protein appeared as a big spot on the gel at a size of 45 kDa when compared with a standard protein molecular weight marker run on the same gel.

The commonly expressed protein was injected in mice. The specific immune response reactive with cancer cells was produced in mice. The humoral immune response was measured by detecting antibodies specific to commonly expressed/over expressed protein. The analysis was performed using standard techniques for westernblot, dot blot and ELISA.

The cellular response (cell mediated immune response=CMI) was measured by enumeration of Interferon gamma and/or granzyme producing cells, and/or % killing of target cells (cancer cells).

The vaccine prepared as per present invention when administered to tumor bearing animals (mice, mammal) results in tumor regression if vaccine and tumor have a same tissue of origin, e.g. melanoma protein vaccine for melanoma.

The following examples illustrate the invention but are in no way limits the scope of invention.

EXAMPLE 1

Method of Identifying the Commonly Expressed Proteins

1. Pancreatic Cancer

The Mia-Pa-Ca-2 cells were treated with Mw Cells in ratio 1:500, cisplatin at 5 µg/ml, paclitaxel at 150 µg/ml, and gemcitabine at 800 nm. The treatment was carried out in serum free media at 37° C. The cells were lysed and SDS-PAGE was run to obtain proteomic profile. Thus obtained profiles were overlapped with the untreated cell protein profile. The protein profile was noticed for each treatment. The differently expressed protein was identified at 45 KDa.

45 KDa protein is commonly over expressed protein when pancreatic cancer cells are treated with Mw, cisplatin, paclitaxel, gemcitabine, or combination there of.

2. Melanoma (Skin Cancer)

The B16 melanoma cells were treated with, cisplatin at 5 µg/ml, paclitaxel at 150 µg/ml, and gemcitabine at 800 nm. The treatment was carried out in serum free media at 37° C. The cells were lysed and SDS-PAGE was run to obtain proteomic profile. Thus obtained profiles were overlapped with the untreated cell protein profile. The protein profile was noticed for each treatment. The differently expressed protein was identified at 36 KDa.

36 KDa protein is commonly expressed protein when melanoma cells are treated with, cisplatin, paclitaxel, gemcitabine, or combination there of.

3. Lung Cancer

Different Lung cancer cell lines (A549 and L132) were treated with Mw/cells in the ratio of 1:100. Each treatment group contained 4×10E6 cells. Cells treated with Mw were incubated for 4 hours at 37° C. After treatment, cells were pelleted and supernatant was discarded. Cells were then resuspended in DPBS (400 µl). Cells were then sonicated for 15 minutes with pulse of 10 seconds on and 20 seconds off. The lysate obtained was estimated for the protein content using BCA Protein assay and protein was normalized to load 30 µg protein in each well. This was followed by 12% reducing SDS PAGE and Western blot analysis to obtain protein profile and humoral response. Thus obtained profile was compared with untreated cell protein profile. Both the cell lines showed a common protein at 43 KDa.

4. Skin Melanoma

Different Skin melanoma cancer cell lines (A375, B16F1 and B16F10) were treated with Mw/cells in the ratio of 1:100. Each treatment group contained 4×10E6 cells. Cells treated with Mw were incubated for 4 hours at 37° C. After treatment, cells were pelleted and supernatant was discarded. Cells were then resuspended in DPBS (400 µl). Cells were then sonicated for 15 minutes with pulse of 10 seconds on and 20 seconds off. The lysate obtained was estimated for the protein content using BOA Protein assay and protein was normalized to load 30 µg protein in each well. This was followed by 12% reducing SDS PAGE and Western blot analysis to obtain protein profile and humoral response. Thus obtained profile was compared with untreated cell protein profile.

The gels showed two proteins one at 36 KDa and second at 170 KDa. Intrestingly both the proteins had cross reactivity between A375, B16F1 and B16F10 when blotted with antibody raised with treated B16 cells while antibodies raised with treated A375 cells only 36 KDa protein was reactive 5. Colon Cancer Different Colon cancer cell lines (HCT15 and Colo205) were treated with Mw/cells in the ratio of 1:100. Each treatment group contained 4×10E6 cells. Cells treated with Mw were incubated for 4 hours at 37° C. After treatment, cells were pelleted and supernatant was discarded. Cells were then resuspended in DPBS (400 µl). Cells were then sonicated for 15 minutes with pulse of 10 seconds on and 20 seconds off. The lysate obtained was estimated for the protein content using BCA Protein assay and protein was normalized to load 30 µg protein in each welt This was followed by 12% reducing SDS PAGE and Western blot analysis to obtain protein profile and humoral response. Thus obtained profile was compared with untreated cell protein profile. Both the cell lines showed a common protein between 10-15 KDa and 26 KDa.

EXAMPLE 2

Method for Isolation of Commonly Expressed/Over Expressed Protein (Cancer Antigen)

Mia-pa ca-2 cell pellet was harvested and washed with sterile DPBS by centrifugation at 2000 rpm for 10 minutes. The cells were treated as in example 1 and 2. Treated cell pellet was re-suspended in DPBS and sonicated for 15 minutes. Total protein content of lysate was estimated by Folin Lowry method. 20 ug of lysate was loaded in each lane of 10% SDS PAGE and run for 45 minutes at 200V. Gel was stained with Coomassie Brilliant Blue R250. 45 KDa band was observed relative to the molecular weight protein marker and sliced out. The sliced piece was chopped fine and incubated in lyses buffer (20 mM Tris —Cl, pH 77, 150 mM NaCl, 0.2% SDS, 2 mM EDTA) on shaking at room temperature overnight. Protein was eluted from gel by centrifuging the lysate at 15000×g for 45 minutes at 4° C. Supernatant was mixed with chilled acetone at 1:4 ratios and incubated at −20° C. for about 1 hour. The obtained precipitate was separated by centrifuging it at 15000*g for 45 minutes at 4° C. Pellet was washed with 3:2 acetone:water solution and centrifuge at 15000*g for 45 minutes at 4° C. Obtained pellet was re-suspended in DPBS and estimated for protein content by Folin Lowry method. Approximately 90% purified protein was obtained.

EXAMPLE 3

Pharmaceutical Formulation

The pharmaceutical formulation of the commonly expressed protein for pancreatic cancer and Melanoma cancer are prepared as below 1. 45 KDa protein from pancreatic cancer cells - 10 µg
   Phosphate buffer     50 mM
   NaCl     150 mM
   Excipeint     qs.
2. 45 KDa protein from pancreatic cancer cells - 50 µg
   Phosphate buffer     50 mM
   NaCl     150 mM
   Excipeint     qs.
3. 45 KDa protein from pancreatic cancer cells - 100 µg
   Phosphate buffer     50 mM
   NaCl     150 mM
   Excipeint     qs.
4. 45 KDa protein from pancreatic cancer cells -10 µg
   Acetate buffer     50 mM
   NaCl     150 mM
   Excipeint     qs.
5. 45 KDa protein from pancreatic cancer cells -50 µg
   Acetate buffer     50 mM
   NaCl     150 mM
   Excipeint     qs.
6. 45 KDa protein from pancreatic cancer cells -100 µg
   Acetate buffer     50 mM
   NaCl     150 mM
   Excipeint     qs.
7. 45 KDa protein from pancreatic cancer cells -100 µg
   Phosphate buffer     10 mM
   NaCl     300 mM
   Excipeint     qs.
8. 45 KDa protein from pancreatic cancer cells -1 µg
   Phosphate buffer     10 mM
   NaCl     300 mM
   Excipeint     qs.
9. 36 KDa protein from melanoma cancer cells-10 µg
   Phosphate buffer     50 mM
   NaCl     150 mM
   Excipeint     qs.
10. 36 KDa protein from melanoma cancer cells-100 µg
   Phosphate buffer     50 mM
   NaCl     150 mM
   Excipeint     qs.
11. 36 KDa protein from melanoma cancer cells-500 µg
   Phosphate buffer     50 mM
   NaCl     150 mM
   Excipeint     qs.
12. 36 KDa protein from melanoma cancer cells-1 µg
   Acetate buffer     50 mM
   NaCl     150 mM
   Excipeint     qs.
13. 36 KDa protein from melanoma cancer cells-500 µg
   Acetate buffer     50 mM
   NaCl     150 mM
   Excipeint     qs.
14. 36 KDa protein from melanoma cancer cells- 50 µg
   Phosphate buffer     10 mM
   NaCl     300 mM
   Excipeint     qs.
15. 45 KDa protein from pancreatic cancer cells-500 µg
   Tris buffer     50 mM
   Excipeint     qs.

-continued

| 16. 36 KDa protein from melanoma cancer cells-500 μg | |
|---|---|
| Tris buffer | 50 mM |
| Excipeint | qs. |

The above formulation is used alone or in combination optionally with adjuvant to elicit desired immune response by appropriate administration.

EXAMPLE 4

Induction of Cell Mediated Immune Response by the Commonly Expressed/Over Expressed Cancer Antigen: Immunogenicity of Cancer Antigen The immunological response to 45 KDa protein (commonly expressed/over expressed) was assessed by immunizing mice intradermally on 0 and 21 day with formulation 1 of example 3, 10 ug of 45 KDa protein. Control mice received PBS. The splenocyte suspension ($10^7$ cells/mL) from individual of the mice was prepared on day 28 of study to estimate IFN-g secreting cells by ELISPOT. ELISPOT assay was performed from splenocytes of both control and test groups.

Figure 1:
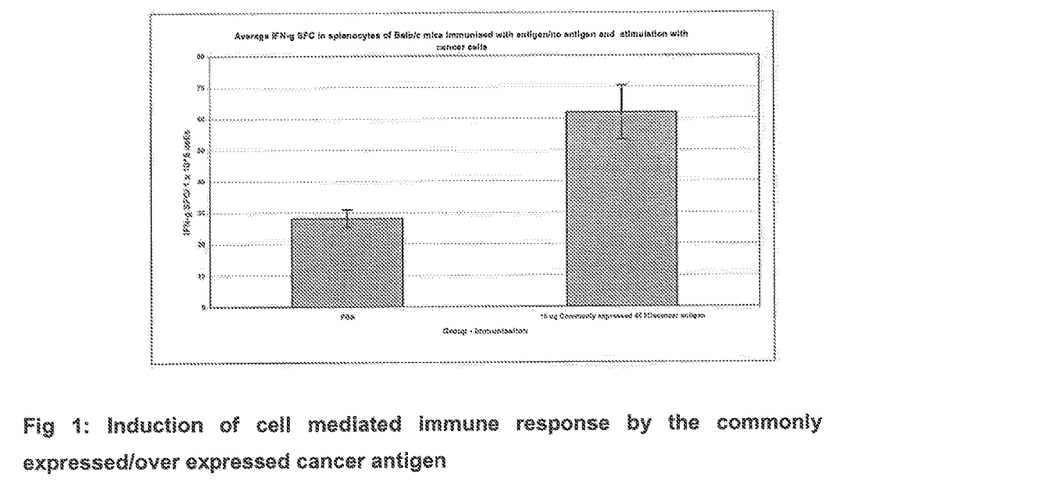
FIG. 1 illustrates induction of cell mediated immune response by the commonly expressed/over expressed cancer antigen.

The image of the plate was captured on the CTL. Spot Reader. The spots in each well were auto-counted. Plate QC was performed by using the sensitivity and background parameters and the results were analyzed. A two fold higher IFN-g release was found in response to 45kDa protein immunization as shown in FIG. 1.

EXAMPLE 5

Figure 2:
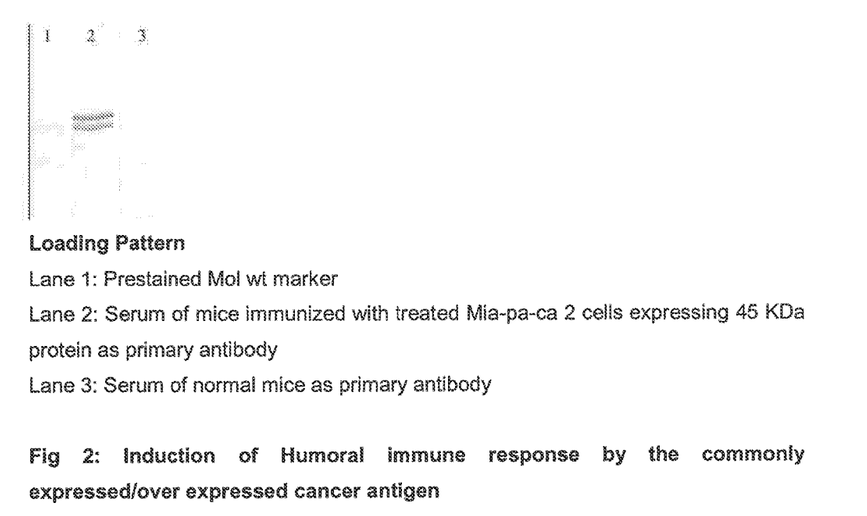
FIG. 2 illustrates induction of humoral immune response by the commonly expressed/over expressed cancer antigen.

Induction of Humoral Immune Response by the Commonly Expressed/Over Expressed Cancer Antigen: Immunogenicity of Cancer Antigen a. The generation of humoral immunity against the cancer antigen was evaluated. Mice were randomized in two groups. First group of mice were immunized intradermally at 0 and 21 day with formulation 15 of example 3, while second group i.e. control group were kept PBS immunized. Serum samples from all of the mice were isolated at 28th day of study to detect the generation of antibody against vaccine. Western blot of MiaPaCa-2 lysate was performed with serum of mice immunised with treated MiaPaCa-2 cancer cells expressing 45 Kda protein and PBS (control). For the detection of primary antibody bound with lysate protein, HRP conjugated goat Anti-mouse IgG antibody was used with DAB (Diamine Benzidine) as coloring agent. From western blot analysis it is found that MiaPaCa-2 cancer vaccine immunization generates antibody response against cancer antigen (FIG. 2).

b. To generate high antibody titers in rabbit the antigen of melanoma cancer formulation 10 of example 3, (36 KDa) was co-administered with Freund's adjuvant on day 0, 7 and 14. The immunized rabbits were bleed on day 21 and antibody titers were measured by dot blot assay by coating the antigen on nitrocellulose membrane and using immunized rabbit sera as primary antibody. The blots were developed by secondary antibody—HRPO conjugate. The titers were found to be more then 10000 for anti-melanoma antigen.

c. To generate anti-pancreatic cancer antigen antibody, rabbits were immunized with pancreatic cancer antigen formulation 8 of example 3, (~45 Kda protein) with Freund's complete adjuvant and on day 15 with Freund's incomplete adjuvant. The immunized rabbits were bleed on day 30 and antibody titers were measured by dot blot assay by coating the antigen on nitrocellulose membrane and using immunized rabbit sera as primary antibody. The blots were developed by secondary antibody—HRPO conjugate. The titers were found to be more then 50000 for anti-Pancreatic cancer antigen.

EXAMPLE 6

In Vitro Killing of Hetrogeneous and Homogeneous Cancer Cells Splenocytes of Immunized Mice: Effector Function Assay A. Immune Response Against Homologus Cancer Cells Male Balb/C mice (6-8 week), 20 in numbers were used for the study. The animals were randomized on the basis of body weight and were divided into 2 groups of 10 animals each. First group of mice were immunized intradermally at 0 and 21 day with cancer antigen formulation 7 of example 3, 100 μg/mice/dose (commonly expressed protein of 45 KDa isolated from treated Mia-pa-ca-2 cells as described in example 1) while second group i.e. control mice were kept PBS immunized.

Splenocytes from immunized animals of respective groups were distributed in polypropylene tubes containing the MiaPaCa-2 cells as target. Splenocyte effectors were added to obtain effector to target ratio of 5:1 and 1:1 respectively. The tubes were incubated at 37° C. and 6% CO2 for 4 hrs. After 4 hrs the cells were pelleted by centrifugation at 300×g for 10 min. The supernatant was discarded and the pellet fixed in 1% (w/v) p-formaldehyde solution and then washed twice with DPBS by centrifugation. 70% ice-cold ethanol was added and the cells were allowed to stand on ice for 30 min. The cells were stored at −20° C. until further analysis.

The cytolytic activity of T-cells was evaluated by determining target cell death by effector cells using the BD APO BrdU Kit protocol. The APO-BRDU kit is a two color staining method for labeling DNA breaks and total cellular DNA to detect apoptotic cells by flow cytometry. The cancer antigen (commonly expressed protein of 45 KDa) immunized mice shows significantly higher lyses of homologus target (Mia-pa-ca-2 cancer cells) cells in comparison to control group at 5:1 (effector:target) ratios.

B. Immune Response Against Heterogenous (Hetrologus) Cancer Cells

Male Balb/C mice (6-8 week), 20 in numbers were used for the study. The animals were randomized on the basis of body weight and were divided into 2 groups of 10 animals each. First group of mice were immunized intradermally at 0 and 21 day with cancer antigen formulation 5 of example 3, 50 μg/mice/dose (commonly expressed protein of 45 KDa isolated from treated Mia-pa-ca-2 cells as described in example 1) while second group i.e. control mice were kept PBS immunized.

Splenocytes from immunized animals of respective groups were distributed in polypropylene tubes containing the Panc-1, AsPC-1 or SW1990 cells as target. Splenocyte effectors were added to obtain effector to target ratio of 5:1 and 1:1 respectively. The tubes were incubated at 37° C. and 6% $CO_2$ for 4 hrs. After 4 hrs the cells were pelleted by centrifugation at 300×g for 10 min. The supernatant was discarded and the pellet fixed in 1% (w/v) p-formaldehyde solution and then washed twice with DPBS by centrifugation. 70% ice-cold ethanol was added and the cells were allowed to stand on ice for 30 min. The cells were stored at −20° C. until further analysis.

The cytolytic activity of T-cells was evaluated by determining target cell death by effector cells using the BD APO BrdU Kit protocol. The APO-BRDU kit is a two color staining method for labeling DNA breaks and total cellular DNA to detect apoptotic cells by flow cytometry. The cancer antigen (commonly expressed protein of 45 KDa) immunized mice shows significantly higher lyses of hetrologus target pancreatic cancer cells (Panc-1, AsPC-1 or SW1990) cells in comparison to control group at 5:1 (effector: target) ratios.

EXAMPLE 7

In Vivo Tumor Regression in Mice Functional Assay

1. Male Balb/C mice (6-8 week), 30 in numbers were used for the study. The animals were randomized on the basis of body weight. The tumor induction was done by injecting $1 \times 10^5$ B16-F1 cells in hind limb of the mice subcutaneously. Mice were allowed to develop average tumor size of ~100-150 mm3 and randomized in 2 groups 10 mice each on basis of tumor size. First group of mice were immunized intradermally with melanoma vaccine formulation 13 of example 3, 500 µg/mice/dose (Commonly expressed 36 KDa protein) at 0 and 10 day post randomization while second group i.e. control mice were kept un-immunized. Tumor size growth was recorded twice a week till the tumor size reached the 10% of animal body weight.

Figure 3:
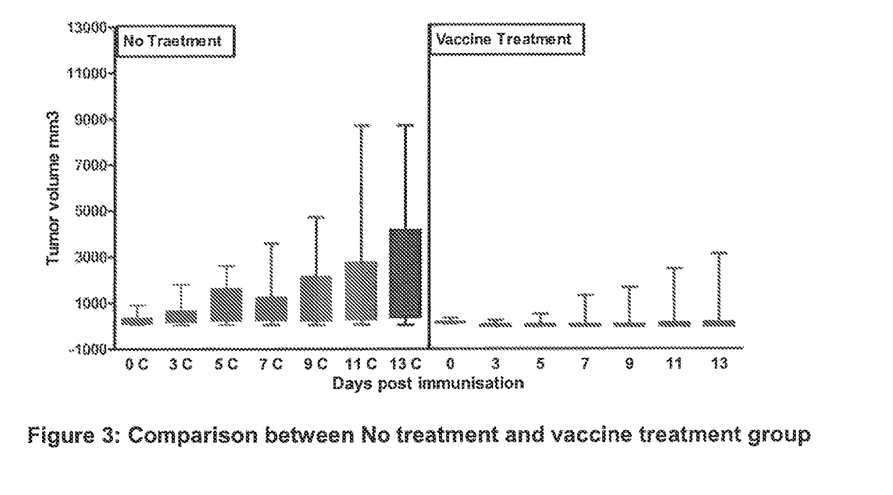
FIG. 3 shows a comparison between No treatment and Vaccine treatment group.

The tumor volume in treatment group did not rise as compared to the untreated group (FIG. 3). The Treatment group in fact showed tumor size reduction indicating the resolution of disease condition. Over all the survival was Improved and tumor size in mice reduced in treatment group.

2. Male C57 mice (6-8 week), 20 in numbers were used for the study. The animals were randomized on the basis of body weight. The tumor induction was done by injecting $1 \times 10^5$ Pan 02 (pancreatic cancer cell line) cells in hind limb of the mice subcutaneously. Mice were allowed to develop average tumor size of ~200 mm3 and randomized in 2 groups 10 mice each on basis of tumor size. First group of mice were immunized intradermally with pancreatic cancer vaccine formulation 4 of example 3, 10 µg/mice/dose (Commonly expressed 45 KDa protein) on 0 and 10 day post randomization while second group i.e. control mice were kept un-immunized (no treatment). Tumor size was recorded twice a week till the tumor size reached the 10% of animal body weight.

The tumor volume in treatment group did not rise as compared to the untreated group. Over all the survival was Improved and tumor size in mice reduced in treatment group. The treatment group showed delayed progression of tumor mass compared to animals with No treatment.

3. Male C57 mice (6-8 week), 10 in numbers were used for the study. The animals were randomized on the basis of body weight. First group of mice were immunized intradermally with pancreatic cancer vaccine formulation 15 of example 3, 500 µg/mice/dose (Commonly expressed 45 KDa protein) on 0 and 10 day post randomization while second group i.e. control mice were kept un-immunized (no treatment). The tumor induction was done by injecting $1 \times 10^5$ Pan 02 (pancreatic cancer cell line) cells in hind limb of the mice subcutaneously on $10^{th}$ day after $1^{st}$ injection of pancreatic cancer vaccine. Tumor size was recorded twice a week till the tumor size reached the 10% of animal body weight.

The tumor volume in treatment group did not rise as compared to the untreated group. Over all the survival was more in treated group. The treatment group showed delayed development of tumor compared to animals with No treatment.

EXAMPLE 8

Figure 4:
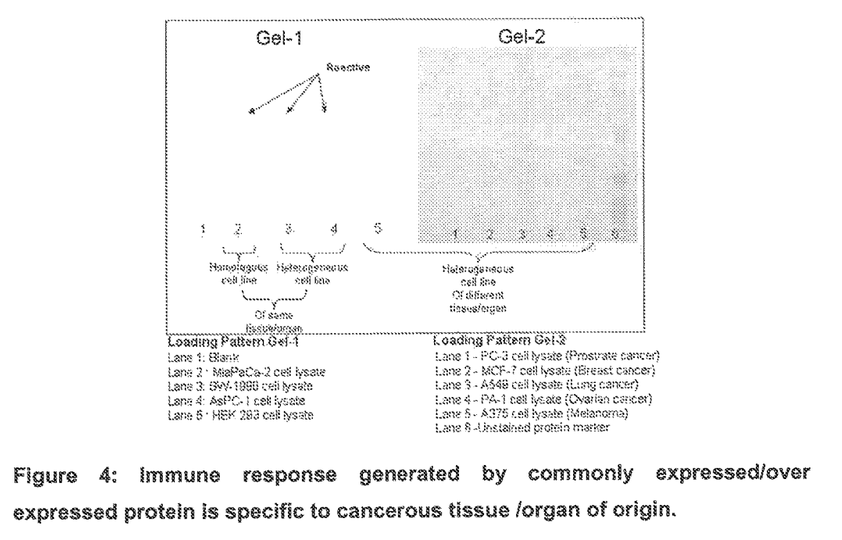
FIG. 4 illustrates immune response generated by commonly expressed/over expressed protein specific to cancerous tissue/organ of origin.

Immune Response Generated by Commonly Expressed/Over Expressed Protein is Specific to Cancerous Tissue/Organ of Origin Mice were immunized intradermally at 0 and 21 day with cancer antigen formulation 5 of example 3, 50 µg/mice/dose (commonly expressed protein of 45 KDa). Serum samples from mice were isolated on $28^{th}$ day of study. Western blot with lysates of MiaPaCa-2, AsPC-1, SW-1990 and cancers of different origin like HEK-293 (Kidney), PC-3 (Prostate), MCF-7 (Breast), A549 (Lung), PA-1 (Ovary) was performed with primary antibody generated in mouse against therapeutic cancer vaccine. For the detection of primary antibody bound with lysate antigen/s, HRP conjugated goat Anti-mouse IgG antibody was used with DAB (Diamino Benzidine) as coloring/detection agent. Western blot analysis shows (FIG. 4) that antibody generated by immunization of (commonly expressed protein of 45 KDa) has heterogeneous reactivity with cancer cell lysates of pancreatic origin (heterogeneous) while it is non reactive with cancer cell lysates of different tissue/organ. In FIG. 4 Gel 1 the lane 2 to 4 are with pancreatic cancer cells of different types showing reactivity with the serum of cancer antigen (commonly expressed protein of 45 KDa) immunized mice indicating hetrogeous reactivity to cancer cells of tissue/organ of origin. While in Gel 2 the lane 1 to 5 shows no reactivity with cancer cells of different tissue/origin viz. Prostate, breast, Lung, Ovary, and Skin illustrating safety of the vaccine containing cancer antigen (commonly expressed protein).

The present invention has surprisingly found that cancer cells treated with cisplatin, paclitaxel, gemcitabine, *Mycobacterium* w or combination there of shows altered protein profile. Further the protein profiles of treated cell is found to have at least one protein common (commonly expressed/over expressed) irrespective agent used for treatment e,g, *Mycobacterium* w, cisplatin, paclitaxel, gemcitabine. The protein (commonly expressed/over expressed) is different for cancer cells originating from different organ/tissue.

The commonly expressed protein as formulated in amount more then 1 µg, is found to be immunogenic and induces immune response reactive against cancer cells from which it is derived (homologous) as well as cancer cells of same tissue/organ but with different cell characteristic (heterologus) as described in example above. The immune response generated using pancreatic cancer cell line fails to generate immune response against other cancer. Administration of the protein/s is found to be safe in mammals. Optionally to obtain even improved immune response these proteins may be combined with adjuvant before administration to a mammal.

The immune response so generated is capable of providing prophylactic as well as therapeutic effects against pancreatic cancer.

We claim:

1. A method of treating cancer in a patient comprising:
   (a) treating cancer cell line derived from the same cancer or tissue type as the patient's cancer with *Mycobacterium* w;
   (b) measuring and comparing protein expression levels between treated untreated cancer cells;
   (c) identifying one or more proteins with increased expression after *Mycobacterium* w treatment as compared to untreated cancer cells; and,
   (d) administering said one or more proteins identified in step (c) to the patient.

2. The method of claim 1, wherein said one or more proteins is a cancer antigen.

3. The method of claim 1, wherein said one or more proteins elicits immune response against said patient's cancer.

4. The method of claim 3, wherein said elicited immune response is cell mediated immune response.

5. The method of claim 3, wherein said elicited immune response is humoral immune response.

6. The method of claim 1 wherein said one or more proteins is immunogenic.

\* \* \* \* \*